(12) United States Patent
Moore et al.

(10) Patent No.: US 7,879,569 B2
(45) Date of Patent: Feb. 1, 2011

(54) METHODS FOR DIAGNOSIS OF MYELODYSPLASTIC SYNDROMES (MDS)

(75) Inventors: Jonni Moore, Moorestown, NJ (US); Sindhu Cherian, Seattle, WA (US); Adam Bagg, Gulph Mills, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 447 days.

(21) Appl. No.: 11/667,406

(22) PCT Filed: Nov. 7, 2005

(86) PCT No.: PCT/US2005/040197

§ 371 (c)(1), (2), (4) Date: May 9, 2007

(87) PCT Pub. No.: WO2006/052842

PCT Pub. Date: May 18, 2006

(65) Prior Publication Data

US 2008/0026406 A1 Jan. 31, 2008

Related U.S. Application Data

(60) Provisional application No. 60/625,942, filed on Nov. 9, 2004, provisional application No. 60/628,537, filed on Nov. 18, 2004.

(51) Int. Cl.
*G01N 33/574* (2006.01)
*G01N 21/66* (2006.01)

(52) U.S. Cl. ............ 435/7.23; 435/7.2; 435/7.24; 435/7.25; 435/287.2; 435/973; 436/10; 436/63; 436/64; 436/164; 436/172; 436/811; 436/813; 422/61; 422/73; 422/82.08; 422/82.09

(58) Field of Classification Search .............. 435/2, 435/7.2, 7.24, 7.25, 287.2, 973, 7.23; 436/518, 436/523, 525, 526, 56, 63, 64, 10, 164, 172, 436/811, 813; 422/50, 61, 73, 82.08, 82.09, 422/101
See application file for complete search history.

(56) References Cited

U.S. PATENT DOCUMENTS

| | | | |
|---|---|---|---|
| 6,365,362 B1 * | 4/2002 | Terstappen et al. | 435/7.23 |
| 7,225,082 B1 * | 5/2007 | Natan et al. | 702/27 |
| 7,537,907 B2 * | 5/2009 | Pankowsky | 435/7.23 |

OTHER PUBLICATIONS

Cherian et al., The utility of flow cytometric analysis of peripheral blood neutrophils in the diagnosis and prognosis of myelodysplastic syndromes, Blood (Nov. 16, 2003) vol. 102, No. 11, pp. 426a).*

* cited by examiner

*Primary Examiner*—Gailene R Gabel
(74) *Attorney, Agent, or Firm*—Pearl Cohen Zedek Latzer, LLP; Mark S. Cohen

(57) ABSTRACT

The present invention relates to methods and kits for diagnosing, ascertaining the clinical course a of myelodysplastic syndrome(MDS) and ascertaining response to a therapy regimen of myelodysplastic syndrome. Specifically the invention provides method and kits useful in the diagnosis and determination of clinical parameters associated with MDS based on surface markers unique to MDS.

25 Claims, 8 Drawing Sheets

METHODS FOR DIAGNOSIS OF MYELODYSPLASTIC SYNDROMES (MDS)

CROSS-REFERENCE TO RELATED APPLICATIONS

This application is a National Phase Application of PCT International Application No. PCT/US05/40197, International Filing Date 7 Nov. 2005, claiming priority of U.S. Provisional Patent Applications, 60/625,942, filed 9 Nov. 2004, and 60/628,537, filed 18 Nov. 2004, all which are incorporated herein by reference in their entirety.

FIELD OF THE INVENTION

This invention provides methods and kits for diagnosing, ascertaining the clinical course of diseases associated with myelodysplastic syndromes (MDS) and ascertaining response to a therapy regimen of diseases associated with a myelodysplastic syndrome. Specifically the invention provides methods and kits useful in the diagnosis and determination of clinical parameters associated with diseases associated with MDS based on patterns of surface marker expression unique to MDS.

BACKGROUND OF THE INVENTION

Myelodysplastic syndromes are a heterogeneous group of clonal hematologic disorders characterized by ineffective hematopoiesis and dysplasia. It is a hematological disease in which genomic abnormalities accumulate in a hematopoiesis stem cell leading to peripheral cytopenias of varying degrees of severity, as a consequence of multilineage differentiation impairment, and, in the early phases, bone marrow (BM) apoptosis. Morbidity and mortality in the disease results from cytopenias or transformation to acute myeloid leukemia, which may both lead to serious infectious diseases, anemia or hemorrhage caused by dysfunction and reduction of blood cells. There are associated cytogenetic abnormalities, including deletions of chromosomes 5, 7, amongst others.

The diagnosis of MDS currently requires a multidisciplinary approach involving hematologic, morphologic and cytogenetic analyses, and may be difficult to render, owing to the fact that at least 50% of patients present with one or fewer cytopenias and only ~50% of patients demonstrate cytogenetic abnormalities.

Flow cytometric analysis in the evaluation of MDS has focused on complex immunophenotypic evaluation of the bone marrow, which entails use of an extensive antibody panel and examining various cell types While the diagnosis is straightforward in some cases, it may also be difficult to render as less than half of patients with MDS have cytogenetic abnormalities and morphologic dysplasia may be subtle. Although studies have suggested a role for flow cytometric (FCM) analysis in the evaluation of MDS, most of these require the complex evaluation of numerous parameters in multiple cell types, typically in the bone marrow.

To date, a single assay or system, involving the analysis of peripheral blood samples for the diagnosis of MDS is lacking. The diagnosis of MDS requires integration of hematology, morphology of the peripheral blood and bone marrow, and cytogenetics. Even with these tools, a diagnosis of MDS may be elusive and there remains a need for additional diagnostic tools

SUMMARY OF THE INVENTION

In one embodiment, the invention provides method of diagnosing a subject with myelodisplastic syndrome (MDS) in a subject, comprising analyzing predictive parameters in a blood sample of said subject; comparing the predictive parameters to a control; and assigning a numerical score to the values obtained, wherein a score of about 2 or greater indicates said subject suffers from myelodysplastic syndromes.

In another embodiment, the invention provides a method of quantifying in a subject the severity of myelodysplastic syndrome in a subject, comprising: analyzing predictive parameters in leukocytes from a blood sample of the subject; comparing the predictive parameters to a control sample; and assigning a numerical score to the values obtained, wherein a score of 3 or greater indicates the severity of said myelodysplastic syndrome.

In one embodiment, the invention provides a method of ascertaining response to a therapy regimen in a subject diagnosed with myelodysplastic syndrome, comprising: analyzing predictive parameters in leukocytes from a blood sample of the subject; comparing the predictive parameters to a control sample taken from said subject obtained prior to the initiation of, or earlier in, said therapy regimen, or a combination thereof; and assigning a numerical score to the values obtained, wherein a decrease in score indicates responsiveness to said therapy regimen.

In another embodiment, the invention provides a kit for a diagnosis of myelodysplastic syndrome (MDS) comprising an antibody, a fragment thereof, or a molecular beacon, said antibody, fragment thereof, or molecular beacon specifically reactive with a cell surface marker predictive of MDS.

DETAILED DESCRIPTION OF THE INVENTION

Figure 1:
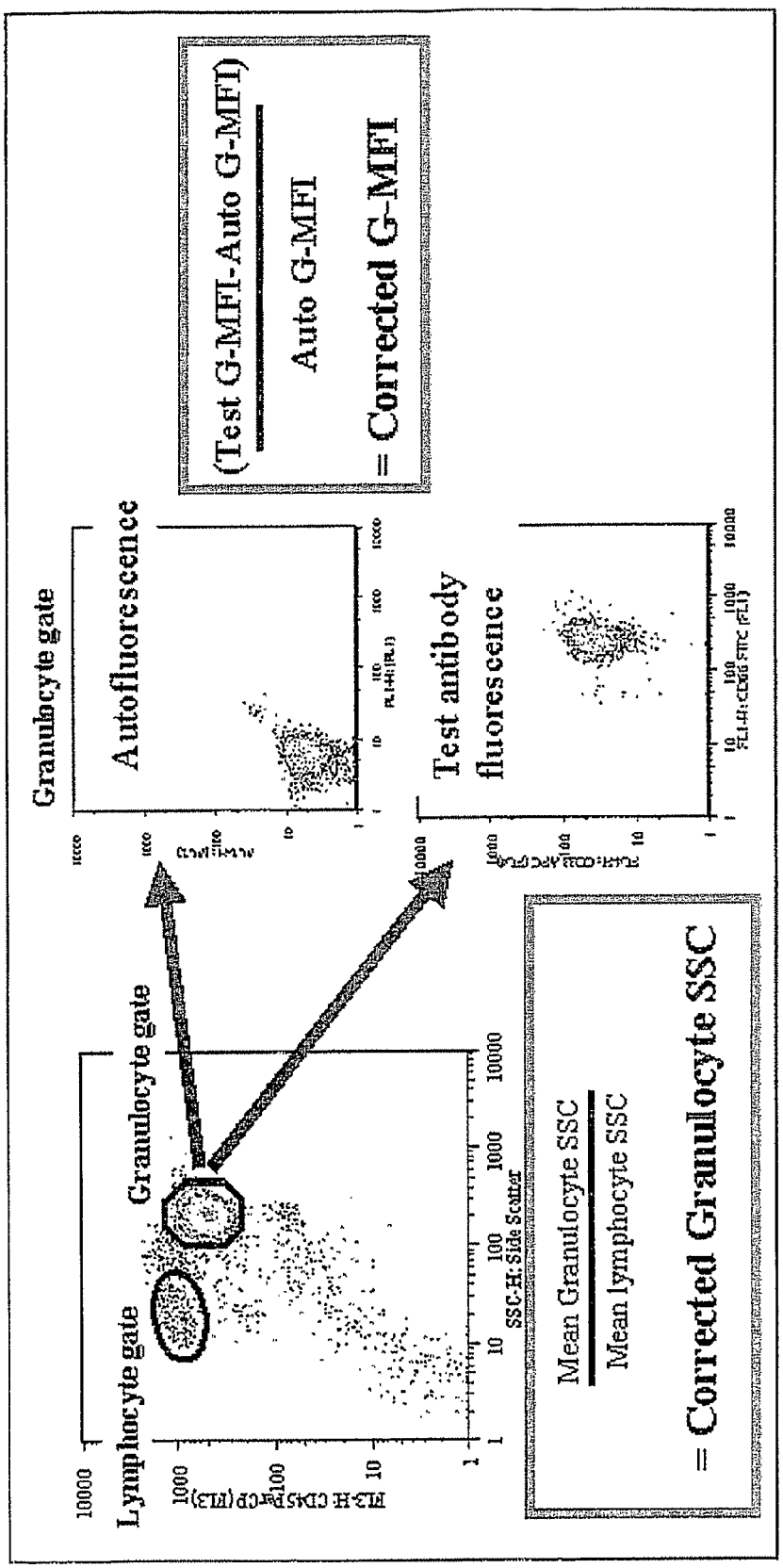
FIG. 1 depicts the gating strategy used in an embodiment of the methods of the invention Lymphocyte and granulocyte gates were drawn based on CD45 versus side scatter characteristics. A geometric fluorescence intensity (G-MFI) was derived for controls for autofluorescence and each antibody assayed. The corrected G-MFI was calculated as illustrated. The mean side scatter was calculated for the lymphocyte and the granulocyte gate and the corrected granulocyte side scatter was calculated.

This invention provides, in one embodiment, methods and kits for assessing myelodysplastic syndrome.

The myelodysplastic syndromes (MDS) are a group of disorders characterized by one or more peripheral blood cytopenias secondary to bone marrow dysfunction. The syndromes may arise de novo, or following treatment with chemotherapy and/or radiation therapy Secondary myelodysplasia usually has a poorer prognosis than does de novo myelodysplasia. Prognosis may be related to the number of bone marrow blast cells and to the degree of peripheral blood cytopenias. The MDS transform to acute myeloid leukemia (AML) in about 30% of patients after various intervals from diagnosis, and at variable rates.

No single effective cure is known, and instead supportive care is the most common treatment. Presently, platelet and blood transfusions are used, in order to favorably affect prognosis in affected subjects.

Classification systems of MDS include the French-American-British (FAB) classification system, and the World Health Organization (WHO) classification system, which rely on the appearance of particular cells in the bone marrow, however, reliance on small differences in appearance for defining a category has resulted in inconsistencies in classification.

In one embodiment, multiparameter flow cytometric analysis of peripheral blood using the PB MDS score is useful in the diagnosis of MDS. Furthermore, the evaluation of only 5 PMN flow cytometric parameters is at least as sensitive as existing subjective (cytogenetic) testing and in another embodiment even more specific for the identification of patients with MDS.

In one embodiment, the methods and kits of the invention maintain the ability to integrate the heterogeneity of phenotypic changes observed in MDS while maintaining a surprising level of simplicity that would allow it to be easily integrated into a clinical flow cytometry laboratory.

Therefore, according to this aspect of the invention and in one embodiment, the invention provides a method of diagnosing a subject with myelodisplastic syndrome (MDS), comprising analyzing predictive parameters in a blood sample of said subject; comparing the predictive parameters to a control; and assigning a numerical score to the values obtained, wherein a score of about 2 or greater indicates said subject suffers from a myelodysplastic syndrome.

In one embodiment, the method of diagnosing results in greater sensitivity than present methods. The term "sensitivity" refers, in one embodiment, to the probability that a positive result obtained by the method correlates with a positive diagnosis of the patient, that is that when a "true positive" is obtained, the subject is indeed suffering from myelodysplastic syndrome (MDS).

In another embodiment, the method of diagnosing results in greater specificity than present methods. The term "specificity" refers, in one embodiment, to the probability that a negative result obtained by the method correlates with a negative diagnosis of the patient, that is that a "true negative" is obtained, the subject does not have MDS. In one embodiment the methods and kits of the invention provide diagnosis with 73% sensitivity and 90% specificity.

In one embodiment, the method comprises obtaining a blood sample from a subject and analyzing predictive parameters in leukocytes from the blood sample obtained from the subject.

The obtaining of a blood sample is via means well known in the art, as is the analysis specifically of a leukocyte population. In one embodiment, the analysis is conducted on blood samples enriched for leukocytes, such as, via the obtaining of a "buffy coat", as will be readily appreciated by one skilled in the art. In one embodiment, leukocyte rich fractions may be prepared from whole blood via differential centrifugation, with the use, for example, of a sucrose gradient, or in another embodiment, via Ficoll-hypaque density centrifugation. In another embodiment, both buffy coats may be further subjected to density gradient centrifugation.

In another embodiment, the analysis is conducted on leukocytes in blood samples, which have not undergone any leukocyte enrichment.

In another embodiment, the method further comprises the step of lysing red blood cells from the blood sample, which in another embodiment, is enriched for leukocytes. In another embodiment, the analysis of predictive parameters is conducted on neutrophils in the sample.

According to this aspect of the invention, analysis of predictive parameters comprises analyzing cell granularity and expression of at least one cell surface marker.

In one embodiment, the predictive parameters assessed by the methods of this invention include, but are not limited to, cellular biomarkers, such as, for example, cell surface markers or cell granularity. In one embodiment, the predictive parameters detected by the methods and kits of the invention, are a cell granularity parameter and the expression of a cell surface marker.

In one embodiment, the predictive parameters comprise CD66, CD11a, CD10, CD116, or any combination thereof.

CD66 is a member of the carcinoembryonic antigen family of proteins that is expressed on various tissue types. On neutrophils, CD66 may be correlated with activation and with increased CD11/CD18 mediated cellular adhesion, which may therefore be related to increased PMN activation in patients with MDS.

"CD11a" refers, in one embodiment, to the alpha subunit of LFA-1, an adhesion molecule, from any mammal, such as, in another embodiment, from a human.

Patients with early MDS appear to have accelerated apoptosis of myeloid cells, while more advanced categories of disease have a decrease in apoptotic activity and an increase in cell proliferation. The alterations in CD10 expression in MDS exemplified herein may reflect abnormal apoptosis, as CD10 may be a marker of apoptosis.

CD116, the alpha chain of the granulocyte-macrophage colony stimulating factor (GM-CSF) receptor, was diminished in 2 patients and increased in 1 patient with MDS, as exemplified herein, and thus, in another embodiment, serves as a predictive parameter for MDS, in the methods of this invention.

In one embodiment, analysis of the predictive parameters is via the use of an antibody. In one embodiment, analysis is via the use of an antibody specific for CD66, CD11a, CD10, CD116, or any combination thereof. In another embodiment, analysis is via the use of an antibody specific for CD45.

The term "antibody" is used in the broadest sense and covers, in other embodiments, monoclonal antibodies (including full length monoclonal antibodies), polyclonal antibodies, multispecific antibodies (e.g., bispecific antibodies), antibody fragments, or combinations thereof, as will be readily appreciated by one skilled in the art.

Antibodies of the invention bind selectively to predictive parameters in the blood sample of the subject, which are in another embodiment CD66, or CD11a, CD10, CD116, CD45 or a combination thereof in other embodiments. In one embodiment, the term "antibody" include complete antibodies (e.g., bivalent IgG, pentavalent IgM) or fragments of antibodies in other embodiments, which contain an antigen binding site. Such fragment include in one embodiment Fab, $F(ab')_2$, Fv and single chain Fv (scFv) fragments. In one embodiment, such fragments may or may not include antibody constant domains. In another embodiment, Fab's lack constant domains which are required for complement fixation. scFvs are composed of an antibody variable light chain ($V_L$) linked to a variable heavy chain ($V_H$) by a flexible linker. scFvs are able to bind antigen and can be rapidly produced in bacteria. The invention includes antibodies and antibody fragments which are produced in bacteria and in mammalian cell culture. An antibody obtained from a bacteriophage library can be a complete antibody or an antibody fragment. In one embodiment, the domains present in such a library are heavy chain variable domains ($V_H$) and light chain variable domains ($V_L$) which together comprise Fv or scFv, with the addition, in another embodiment, of a heavy chain constant domain ($C_{H1}$) and a light chain constant domain ($C_L$). The four domains (i.e., $V_H$-$C_{H1}$ and $V_L$-$C_L$) comprise an Fab. Complete antibodies are obtained in one embodiment, from such a library by replacing missing constant domains once a desired $V_H$-$V_L$ combination has been identified.

Antibodies of the invention can be monoclonal antibodies (Mab) in one embodiment, or polyclonal antibodies in another embodiment. Antibodies of the invention which are useful for the compositions, methods and kits of the invention can be from any source, and in addition may be chimeric. In one embodiment, sources of antibodies can be from a mouse, or a rat, or a human in other embodiments. Antibodies of the invention which are useful for the compositions, methods and kits of the invention have reduced antigenicity in humans, and in another embodiment, are not antigenic in humans. Chimeric antibodies for use the invention contain in one embodiment, human amino acid sequences and include humanized antibodies which are non-human antibodies substituted with sequences of human origin to reduce or eliminate immunogenicity, but which retain the binding characteristics of the non-human antibody.

The antibody used may be conjugated to a detectable label, which, in another embodiment is fluorescent. In one embodiment, when the analysis of the predictive parameters is for several biomarkers simultaneously, labeled antibodies may be used, and in one embodiment, the labels will be individually discernable, such as, for example, in the use of multiple fluorescent labels whose emission spectra do not overlap.

The term "detectable label" refers in one embodiment to a composition or moiety that is detectable by spectroscopic, photochemical, biochemical, immunochemical, electromagnetic, radiochemical (using technetium-99m ($^{99m}$Tc) e.g.), or chemical means such as fluorescence, chemifluoresence, or chemiluminescence, or any other appropriate means. In another embodiment, detectable labels are fluorescent dye molecules, or fluorophores, such fluorescein, phycoerythrin, CY3, CY5, allophycocyanine, Texas Red, peridenin chlorophyll, cyanine, FAM, JOE, TAMRA, TET, VIC. Methods and compositions for detectably labeling molecules, such as oligonucleotides, DNA-RNA hybrids, etc. are well known in the art. See, e.g., U.S. Pat. Nos. 6,316,230; 6,297,016; 6,316,610; 6,060,240; 6,150,107; and 6,028,290, each of which are hereby incorporated by reference in their entirety.

In one embodiment, the photoluminescent dye used in the beacons, methods and kits of the invention is fluorescein, phycoerythrin, CY3, CY5, allophycocyanine, Texas Red, peridenin chlorophyll, cyanine, FAM, JOE, TAMRA, TET, VIC, or a combination thereof. In another embodiment, the FAM is 6-carboxyfluorescein (6-FAM).

In one embodiment, cell granularity is a predictive parameter. In one embodiment, cell granularity is assessed as a function of cell surface expression of CD45. CD45 is a membrane-bound protein tyrosine phosphatase (PTP) expressed in various isoforms, of between 180 and 220 kD in size. CD45 is expressed on virtually all leukocytes, including myeloid and lymphoid precursors in bone marrow and mature lymphocytes in lymph nodes. According to this aspect of the invention, and in one embodiment, analysis of cell granularity may be via the use of an antibody specific for CD45. It is to be understood that embodiments for antibodies used for analysis of predictive parameters, as described herein, are applicable for analysis of any predictive parameter, including cell surface molecule expression, which may, in another embodiment, reflect cell granularity.

In another embodiment, the method employs flow cytometry. In another embodiment, in a peripheral blood sample, lymphocyte, monocyte and granulocyte populations can be defined on the basis of forward and side scatter. Forward and side scatter are used in one embodiment to exclude debris and dead cells.

Flow cytometry is an optical technique that analyzes particles or cells in a fluid mixture based on their optical characteristics, via the use of a flow cytometer (See, for example, Shapiro, "Practical Flow Cytometry," Third Ed. (Alan R. Liss, Inc., 1995); and Melamed et al., "Flow Cytometry and Sorting," Second Ed. (Wiley-Liss 1990)). Flow cytometers hydrodynamically focus a fluid suspension of particles/cells into a thin stream so that they flow down the stream in substantially single file and pass through an examination zone. A focused light beam, such as a laser beam illuminates the particles as they flow through the examination zone. Optical detectors within the flow cytometer measure certain characteristics of the light as it interacts with the particles/cells Commonly used flow cytometers such as the Becton-Dickinson Immunocytometry Systems "FACSCAN" (San Jose, Calif.) can measure forward light scatter (generally correlated with the refractive index and size of the particle/cell being illuminated), side light scatter (generally correlated with the cell granularity), and particle fluorescence at one or more wavelengths Multiparameter cell sorting, that is the simultaneous analysis of multiple predictive parameters, may be used as part of the methods of this invention, and such use will be known to those of skill in the art in light of the present disclosure. In one embodiment, the population of cells to be analyzed is contacted with a panel of antibodies directed against distinct cell surface molecules, under conditions effective to allow antibody binding. The antibodies employed may, in another embodiment, be monoclonal antibodies, and may, in another embodiment, be labeled in a manner to allow their subsequent detection, such as by tagging with a fluorescent label.

For example, one may use fluorochromes that can be excited by 2 different lasers to give off light at 4 different wavelengths, with the potential, in another embodiment, for simultaneous analysis of 4 different surface antigens. In another embodiment, 2 light scattering parameters, direct and orthogonal, or side-scattering capability may be analyzed concurrently, which allows for cell separation on the basis of 6, or 7 parameters. Subsequent cell sorting may be performed, in another embodiment, using fluorescence-activated flow cytometry, by methods well described in the art.

In one embodiment, decreased side scatter represents the morphologically appreciated hypogranularity of granulocytes, such as PMNs in patients with MDS, which serves as a predictive parameter herein.

In one embodiment, combining data regarding side scatter and 4 immunophenotypic variables, allows for the creation of a score, which serves as a multivariate predictor.

The method used in the invention and the kits of the invention employed in their administration comprises the assigning of a numerical score, which serves as a predictive index, in one embodiment, for diseases associated with MDS. In one embodiment, the score the variance of the mean values obtained for the predictive parameters of the test blood sample from the mean value of the same predictive parameters in the control sample. In another embodiment, the score reflects the magnitude of the difference in standard deviation from the mean of at least one predictive parameter from the subject as compared to the control sample.

In one embodiment, points are assigned to a sample, which exhibits statistically significant differences from control values, where the number of points assigned reflects the variance in values obtained, in terms of the number of standard deviations exhibited from the mean value of the control concurrently analyzed.

In one embodiment, statistically significant differences in some predictive parameters are assigned one point for variations in values obtained in terms of mean fluorescence intensity (as determined by FACS analysis of neutrophils expression of cell surface markets, for example) for the sample, if the value correlates with that of one or two standard deviations from the mean value obtained for the control. In another embodiment, if the mean value obtained for the sample correlates with more than two standard deviations from the mean value obtained for the control, then two points may be assigned.

In another embodiment, specific predictive parameters may be assigned a greater number of points, for a smaller variance of values obtained from the sample, in comparison to that obtained from controls.

In one embodiment, differences in side scatter capabilities (SSC) of CD11a, or CD66 expression in samples, which are 1 or 2 standard deviations (SD) from the control mean value, is assigned 1 point. For example, such a difference in SSC, CD11a and CD66 expression will result in the assignment of an MDS score of 3. In another embodiment, any difference in CD10 or CD116 expression, such as loss or abnormal expression, may be assigned two points. For example, such a difference in CD10 and CD116 expression, alone, would result in the assignment of an MDS score of 4.

In one embodiment, a score of about 2 or greater indicates said subject suffers from myelodysplastic syndrome.

As exemplified herein, the assay is relatively non-invasive, as it is performed on peripheral blood. In other embodiments, the methods of this invention may be easily performed in a clinical flow cytometry laboratory.

Using the peripheral blood (PB) MDS score patients may be distinguished from controls with a high level of accuracy ($p<0.005$, in the provided examples). Validation of the scoring system in a test set of patients with cytopenias and/or hematopoietic and the potential of the methods of this invention for use in differentiating MDS from other hematologic conditions is evident.

The skilled artisan will understand that, while in certain embodiments comparative measurements are made of the same predictive parameter at multiple time points, and the score may further reflect such changes in value, as a function of time. In another embodiment, analysis of different predictive parameters is conducted over a time course, such that one parameter is measured at one timepoint, and a second parameter at a second timepoint, and the relative variances of each at a given time may be reflected in the score as well. Similarly, the skilled artisan will understand that serial measurements and changes in values obtained for the predictive parameters, or the combined result over time may also be reflected by the MDS score, and may serve to provide diagnostic and/or prognostic value.

In another embodiment, this invention provides a method of ascertaining the clinical course of a myelodysplastic syndrome, comprising the steps of: obtaining a blood sample from a subject; analyzing predictive parameters in leukocytes from said blood sample, wherein the predictive parameters comprise: cell granularity and expression of at least one cell surface marker; comparing the predictive parameters in the previous step to that in a control sample, a sample from a subject with early stage disease, or a combination thereof; and assigning a numerical score to said sample; wherein said score reflects the variance of the values obtained for said predictive parameters of said sample from that of said control sample, sample from said subject with early stage disease, or a combination thereof; and whereby a score of 3 or greater indicates the severity of said myelodysplastic syndrome, thereby being a method of ascertaining the clinical course of a myelodysplastic syndrome.

In one embodiment, diagnosing MDS, refers to ascertaining the clinical course of myelodysplastic syndrome in a subject. In one embodiment, the phrase "ascertaining the clinical course of myelodysplastic syndrome" refers to any means whereby it is possible to determine the onset, or in another embodiment, severity, or in another embodiment, progression, or in another embodiment, entry into remission, or in another embodiment, development of complications due to myelodysplastic syndrome, or changes in any of these stages.

In one embodiment, the methods of this invention indicate a probability that the subject is afflicted with myelodysplastic syndrome, which may be referred to, in another embodiment, the diagnostic capability of the methods and the MDS score. In another embodiment, the methods of this invention indicate the severity of disease in a subject afflicted with a myelodysplastic syndrome. In another embodiment, the methods of this invention indicate a probability of recovery, or in another embodiment, response to therapy, or in another embodiment, development of neoplasia, or in another embodiment, asymptomatic period, experienced by the subject. In one embodiment, the methods and score system of this invention provide a means of determining the subject's prognosis.

In one embodiment, the phrase "determining the prognosis" refers to the accuracy with which the skilled artisan can predict the course or outcome of the condition in the subject. In one embodiment, the term "prognosis" need not reflect an ability to predict the course or outcome of a condition with 100% accuracy, or in another embodiment, may reflect an ability to predict that a given course or outcome is more likely to occur than not. In another embodiment, the term "prognosis" refers to an increased probability that a certain course or outcome will occur; that is, that a course or outcome is more likely to occur in a patient afflicted with a myelodysplastic syndrome, when compared to those individuals not thus afflicted. In one embodiment, a prognosis is about a 5% chance of a given outcome, or, in another embodiment, about a 7% chance, or, in another embodiment, about a 10% chance, or, in another embodiment, about a 12% chance, or, in another embodiment, about a 15% chance, or, in another embodiment, about a 20% chance, or, in another embodiment, about a 25% chance, or, in another embodiment, about a 30% chance, or, in another embodiment, about a 40% chance, or, in another embodiment, about a 50% chance, or, in another embodiment, about a 60% chance, or, in another embodiment, about a 75% chance, or, in another embodiment, about a 90% chance, or, in another embodiment, about a 95% chance.

It should be understood, that the use of the term "about" refers, in one embodiment to +/−1%, or in another embodiment, +/−2%, or in another embodiment, +/−3%, or in another embodiment, +/−4%, or in another embodiment, +/−5%, or in another embodiment, +/−7% or in another embodiment, +/−10%, or in another embodiment, +/−15%.

The skilled artisan will understand that associating a prognostic indicator with a predisposition to an adverse outcome is a statistical analysis. For example, an MDS Score of 2 or more may signal that a subject is more likely to suffer from an adverse outcome than patients with a score of 1 or less, as determined by a level of statistical significance.

In one embodiment, the invention provides methods and kits for the diagnosis of diseases associated with myelodysplastic syndromes (MDS), referring in another embodiment to acquired hematopoietic stem cell disorders, characterized by cytologic dysplasia in the bone marrow and blood and by various combinations of anemia, neutropenia, and thrombocytopenia, such as refractory cytopenia with multilineage dysplasia (RCMD) in one embodiment, or refractory anaemia (RA), refractory anaemia with ring sideroblasts (RARS), refractory anaemia with excess blasts (RAEB), refractory anaemia with excess blasts in transformation (RAEB-t), chronic myelomonocytic leukaemia (CMML), atypical chronic myelogenous leukemia (aCML), 5q-syndrome.

In one embodiment, refractory cytopenia with multilineage dysplasia (RCMD), refers to a myelodysplastic syndrome (MDS) disease, with bi- or pancytopenia, and dysplastic changes in 10% or more of the cells, in two or more myeloid cell lines (granulocytes, erythroid, or megakaryocytes). There are <1% blasts in the blood and less than 5% blasts in the bone marrow. Auer rods are not present and monocytes in the blood are $<1\times10^9$/L. In another embodiment, if ringed sideroblasts are more than 15% of the erytlroid precursors, the designation of Refractory cytopenia with multilineage dysplasia and ringed sideroblasts (RCMD-RS) is made. In one embodiment, the methods and kits of the invention are used to diagnose RCMD-RS. In one embodiment, the control sample used in the methods and kits of the invention are taken from a subject, or pool of subjects diagnosed and validated as having refractory cytopenia with multilineage dysplasia (RCMD), or RCMD-RS in another embodiment.

For a subject diagnosed with RCMD, blasts account in one embodiment for fewer than 1% of the white cells in the blood, and monocytes are $<1\times10^9$/L. In the bone marrow, blasts number fewer than 5% of the marrow cells, and Auer rods are not found. Dysplastic chances are present in >10% of the cells in two or more myeloid cell lines. In one embodiment, a subject having RCMD will exhibit dysplasia, which is often marked in one or more of the lineages. Neutrophils in the blood or bone marrow show hypogranulation of their cytoplasm or nuclear abnormalities, including nuclear hyposegmentation (pseudo Pelger-Huet change) or bizarrely segmented nuclei. Erythroid precursors in the bone marrow show in one embodiment cytoplasmic vacuoles, nuclear irregularity with multilobation, multinucleation, and megaloblastoid nuclei. When ringed sideroblasts are not seen or account for fewer than 15% of the erythroid precursors, the designation of RCMD is made. When, in another embodiment, 15% or more of the erytluoid precursors are ringed sideroblasts, the diagnosis of RCMD-RS is made. Megakaryocytic abnormalities include in one embodiment, hypolobation of nuclei, widely separated nuclear lobes, or micromegakaryocytes.

In one embodiment, refractory anemia (RA) refers to a myelodysplastic syndrome (MDS) disease, where the subject exhibits less than 5% primitive blood cells (myeloblasts) in the bone marrow and pathological abnormalities primarily seen in red cell precursors. In one embodiment, the control sample used in the methods and kits of the invention are taken from a subject, or pool of subjects diagnosed and validated as having refractory anemia (RA), wherein the corresponding predictive markers, which are the cell markers CD66, CD11a, CD10, CD116, CD45 or a combination thereof, correspond to a blood sample showing less than 5% primitive blood cells (myeloblasts) in the bone marrow and pathological abnormalities in red cell precursors.

In one embodiment, acquired idiopathic sideroblastic anemia (AISA), refers to a myelodysplastic syndrome (MDS) disease, characterized by inadequate formation of heme and excessive accumulation of iron in erythroblast mitochondria. In one embodiment, subjects diagnosed with AISA exhibit normal leucocyte and platelet counts, combined with erythroid hyperplasia, marked dyserythropoiesis and more than 20% ringed sideroblasts. In one embodiment, patients exhibit anemia, normochromic-normocytic, very low retic count, normal platelets and WBC count; marrow analysis exhibit erythroid hyperplasia, dominant ringed sideroblasts (>15% of erythroblasts), decreased colony forming capacity, with about 20% having karyotypic abnormalities as well as some chromosomal abnormalities. In one embodiment, the control sample used in the methods and kits of the invention are taken from a subject, or pool of subjects diagnosed and validated as having idiopathic sideroblastic anemia (AISA).

In one embodiment, refractory anaemia with ring sideroblasts (RARS), refers to a myelodysplastic syndrome (MDS) disease, characterized by less than 5% primitive blood cells (myeloblasts) in the bone marrow and pathological abnormalities primarily seen in red cell precursors in combination with the subject not being responsive to iron supplementation treatment. In addition red cell precursors are unable to use iron normally and in one embodiment, the iron is deposited in characteristic rings in the red cell precursors. These cells are called ring sideroblasts. When, in one embodiment, there are more than 15% ring sideroblasts in the bone marrow the MDS, diagnosed by the kits and methods of the invention is classified as RARS. While anaemia is the most common clinical problem in one embodiment, the numbers of white cells or platelets is also lower than normal in another embodiment of the diagnosis of a subject screened with the methods and kits of the invention, where, in another embodiment, the control sample used in the kits and methods of the invention is taken from a subject or pool of subject exhibiting lower WBC or platelets or both.

In one embodiment, refractory anaemia with excess blasts (RAEB), refers to a myelodysplastic syndrome (MDS) disease, characterized by an increase in precursor blood cells (called blasts) in the marrow to between 5-20% blast cells as well as reduced numbers of platelets or white cells as well as red cells in their blood. When in one embodiment, a higher proportion of blasts (20-30%) is present in the marrow, the diagnosis is refractory anaemia with excess blasts in transformation (RAEB-t). In another embodiment, the control sample used in the methods and kits of the invention is obtained from a subject or pool of subjects having symptoms consistent with RAEB or in another embodiment with RAEB-t.

In one embodiment, chronic myelomonocytic leukaemia (CMML), diagnosed using the methods and kits of the invention, refers to a myelodysplastic syndrome (MDS) disease, characterized by an absolute monocytosis of $>1\times10^9/l$, increased numbers of monocytes in bone marrow, and a variable degree of dysplasia in all three lineages. Myeloblasts, monoblasts and promonocytes comprise less than 5% of nucleated cells in peripheral blood and less than 20% of cells in bone marrow and an absence of the BCR/ABL genetic abnormality. In one embodiment, half of patients present with an elevated white cell count that is commonly associated with hepatomegaly and splenomegaly, the so-called myeloproliferative form of the disease. Patients lacking these features are considered in another embodiment to have the myelodysplastic form of the disease.

In another embodiment, dysplasia involving one or more myeloid lineages or, if myelodysplasia is absent or minimal, either an acquired clonal cytogenetic bone marrow abnormality or at least 3 months of persistent peripheral blood monocytosis, is present if all other causes air ruled out qualifying the symptoms as one of the other MDS diseases. In one embodiment, controls samples used in the methods and kits of the invention, further comprise standard to differentiate the myelodysplastic CMML from the myeloproliferative caused CMML.

In one embodiment, the methods and kits of the invention are useful in diagnosing MDS-associated diseases caused by deletions on the 5q chromosome. These are erythroid dysplasia, or thrombocytosis, hypolobated micromegakaryocytic hyperplasia, or a combination thereof in other embodiments.

In one embodiment, changes in MDS score as a function of time may be reflective of patient prognosis, and, in another embodiment, the degree of change may be related to the severity of adverse events, or in another embodiment, to In one embodiment, this invention provides a method of quantifying in a subject the severity of myelodysplastic syndrome in a subject, comprising: analyzing predictive parameters in leukocytes from a blood sample of the subject; comparing the predictive parameters to a control sample; and assigning a numerical score to the values obtained, wherein a score of 3 or greater indicates the severity of said myelodysplastic syndrome.

Treatment regimens may include, in some embodiments, non-myeloblative bone marrow transplants, using low-does chemotherapy, 5-azacytidine, thalidomide, Trisenox®, Vidaza, combinations thereof, or any proposed regimen, wherein the MDS score and methods of use thereof are indicative of the efficacy of treatment, such as, for example, wherein statistical significance is achieved, in terms of differences in even a single predictive parameter, as described.

In one embodiment, the invention provides a method of ascertaining response to a therapy regimen in a subject diagnosed with myelodysplastic syndrome, comprising: analyzing predictive parameters in leukocytes from a blood sample of the subject; comparing the predictive parameters to a control sample taken from said subject obtained prior to the initiation of, or earlier in, said therapy regimen, or a combination thereof, and assigning a numerical score to the values obtained, wherein a decrease in score indicates responsiveness to said therapy regimen Statistical significance is determined, in other embodiments, by conducting pairwise comparisons, and determining a p value. See, e.g., Dowdy and Wearden, Statistics for Research, John Wiley & Sons, New York, 1983. In one embodiment, a p value of 0.1, 0.05, 0.025, 0.02, 0.01, 0.005, 0.001, 0.0001, or less is indicative of a significant difference.

In the methods and systems according to embodiments of the present invention, data relating to values obtained for the predictive parameters for the sets of diseased and non-diseased samples analyzed may be provided in a database such as Microsoft Access, Oracle, other SQL databases or simply in a data file. The database or data file may contain, for example, a patient identifier such as a name or number, the values obtained, patient prognosis, age of onset of symptoms, therapy regimen, and other identifying and relevant characteristics, as will be understood by one skilled in the art. The database may contain, in other embodiments, the change in MDS Score, as a function of time, or treatment regimen, or a combination thereof.

The methods and scoring systems of this invention may also be used to determine a probability of recurrence of MDS, or, in another embodiment, a probability of progression to AML. Recurrence may be characterized as an increased cytopenia, or other clinical parameters associated with MDS.

In one embodiment, the methods of this invention may further comprise accessing a memory storing the obtained values for the predictive parameters, the MDS score, and other data as listed herein. In another embodiment, the methods of this invention may further comprise generating and graphically displaying the values obtained. In one embodiment, the analysis is executed by a processor or a virtual computer program.

The skilled artisan would readily recognize that it is the intention of the invention to supply kits which will be able to carry out any of the methods embodied herein.

According to this aspect of the invention, and in one embodiment, the invention provides kit for a diagnosis of a myelodysplastic syndrome (MDS) comprising an antibody, a fragment thereof, or a molecular beacon, where the antibody, fragment thereof, or molecular beacon specifically reactive with a cell surface marker predictive of MDS. In one embodiment, the cell surface marker predictive of MDS is any cell marker used in connection with any of the method embodiments described herein. In one embodiment, the cell markers with which the antibody, fragment thereof, or molecular beacon are specifically reactive with are CD66, CD11a, CD10, CD116, CD45 or a combination thereof.

In one embodiment, the kits of the invention may further comprise positive or negative standards, wherein the standard can be assayed and compared to the test sample. It is to be understood that the kits of the invention may be modified and marketed for particular use, which in one embodiment are RAEB-specific, or RAEB-t specific or CMML specific in other embodiments.

In one embodiment, the results obtained are compared to a standard, which, in another embodiment, may comprise a series of standards, which, in another embodiment is used in the kits of the invention for quantification of differential expression. In one embodiment, the standard may comprise any embodiment listed herein, or in another embodiment, will be suitable for a particular application of the kit.

In one embodiment, the standard used is obtained from a subject, or pool of subjects, without any myelodysplastic syndrome (MDS). In another embodiment, the standard is obtained from a subject, or pool of subjects, with myelodysplastic syndrome (MDS).

In one embodiment, the kit of the invention may further comprise a software package contained on a computer storage medium, with a program for correlating values obtained with a standard, for storing and comparing, by date, or in another embodiment for extrapolating results obtained.

In one embodiment the software incorporates statistical tools for determining the significance of the findings. Statistical significance is determined, in other embodiments, by conducting pairwise comparisons, and determining a p value. See, e.g., Dowdy and Wearden, Statistics for Research, John Wiley & Sons, New York, 1983. In one embodiment, a p value of 0.1, 0.05, 0.025, 0.02, 0.01, 0.005, 0.001, 0.0001, or less is indicative of a significant difference.

In one embodiment, the antibody, fragment thereof, or molecular beacon, used in the kits of the invention is detectably labeled. In another embodiment, detectably labeled refers to the conjugation of the antibody, a fragment thereof, or a molecular beacon with a radiolabel, a fluorophore, a peptide, an enzyme, a quantum dot, or a combination thereof.

In one embodiment, the kits and methods of the invention use molecular beacons labeled with colloidal quantum dots. Colloidal quantum dots (QDs) refer in one embodiment to semiconductor nanocrystals whose photoluminescence emission wavelength is proportional to the size of the crystal. The emission spectra of QDs are narrow, which allows multiwavelength labeling with different sizes of QDs with little overlap. QDs outer surfaces is readily conjugated in another embodiment to the molecular beacons of the invention, resulting in a spectrum of labels that are all excited with a single wavelength. In another embodiment, the QDs used in the invention are CdSe nanocrystals.

In one embodiment QDs of different size are used to label the molecular beacons specific for the genes or encoded proteins of the cell markers used in the methods of the invention, such that an emission fingerprint emerges, which will identify the presence of any combination of the cell markers present in the sample. In one embodiment, the obtained sample emission is compared with a standard fingerprint of a sample taken from a subject with a MDS-associated disease. In another embodiment, emission spectra library of myelodysplastic syndromes (MDS) associated diseases—specific molecular beacons of the invention labeled with the QDs of the invention is used to determine the molecular beacon cocktail necessary to diagnose or differentiate a given MDS subtype. In one embodiment, the kits of the invention comprise specific cocktail of molecular beacons.

In one embodiment, the antibody, a fragment thereof, or a molecular beacon exhibit substantial complementarity to their target sequence, which may be a protein, such as a cell marker, or gene encoding the cell markers used in the methods of the invention described herein in other embodiments. In another embodiment, "complementary" indicates that the oligonucleotide or oligopeptide have a base sequence containing an at least 15 contiguous base region that is at least 70% complementary, or in another embodiment at least 80% complementary, or in another embodiment at least 90% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the antibody, a fragment thereof, or a molecular beacon are sufficiently complimentary to their target sequence, which may be a protein, such as such as a cell marker, or gene encoding the cell markers used in the methods of the invention described herein in other embodiments. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

In one embodiment, the kits of the invention comprise one or more of: packaging materials, instructions for using the components, one or more containers for holding the components, standards for calibrating any antibody, fragment thereof or molecular beacon detection reaction, standard target sequences, or amplification primers for amplifying a target sequence.

In another embodiment, contacting the sample with the kits of the invention, comprises amplifying the target gene encoding the cell markers used in the methods of the invention described herein in other embodiments. In one embodiment, the term "amplification" or "amplify" refers to one or more methods known in the art for copying a target nucleic acid, thereby increasing the number of copies of a selected nucleic acid sequence. Amplification may be exponential in one embodiment, or linear in another. In one embodiment, a target nucleic acid may be either DNA or RNA. The sequences amplified in this manner form an "amplicon." While the exemplary embodiments described herein relate to amplification using the polymerase chain reaction ("PCR"), numerous other methods are known in the art for amplification of nucleic acids (e.g., isothermal methods, rolling circle methods, etc.) and are considered within the scope of the present invention. The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April ; 30(4):852-6, 858, 860 passim; Zhong et al., Biotechniques 2001 April; 30(4):852-6, 858, 860.

In another embodiment, real time PCR is used in the methods of the invention. The term "real time PCR" refers in one embodiment to the process where a signal emitted from the PCR assay is monitored during the reaction as an indicator of amplicon production during each PCR amplification cycle (i.e., in "real time"), as opposed to conventional PCR methods, in which an assay signal is detected at the endpoint of the PCR reaction Real time PCR is based in one embodiment on the detection and quantitation of a fluorescent reporter. The signal increases in direct proportion to the amount of PCR product in a reaction By recording the amount of fluorescence emission at each cycle, it is possible to monitor the PCR reaction during exponential phase where the first significant increase in the amount of PCR product correlates to the initial amount of target template. For a general description of "real time PCR" see Dehe et al. J. Virol. Meth. 102:37-51 (2002); and Aldea et al. J. Clin. Microbiol. 40:1060-1062 (2002) (referring to the "LightCycler," where real-time, kinetic quantification allows measurements to be made during the log-linear phase of a PCR).

In one embodiment, the cells used for the methods of the invention are obtained from a sample given by the subject. The sample to be analyzed may consist in one embodiment of, or comprise blood, bone marrow sample, spleen sample, liver sample, sera, urine, mucosa, feces, epidermal sample, skin sample, cheek swab, sperm, amniotic fluid, cultured cells, bone marrow sample or chorionic villi, and the like. A biological sample may be processed in another embodiment to release or otherwise make available a nucleic acid or a protein for detection as described herein. Such processing may include in one embodiment steps of nucleic acid manipulation, e.g., preparing a cDNA by reverse transcription of RNA from the biological sample. Thus, the nucleic acid to be amplified in one embodiment by the methods of the invention may be DNA or RNA.

In one embodiment, the kits of the invention, used to carry out the methods described herein, are used for detecting the presence of MDS, or quantifying the severity of MDS, evaluating efficiency of treatment regimen for MDS or a combination thereof in other embodiments.

The following examples are presented in order to more fully illustrate the preferred embodiments of the invention. They should in no way be construed, however, as limiting the broad scope of the invention.

EXAMPLES

Materials and Methods

Patients

Peripheral blood samples from 15 patients with a diagnosis of MDS (n=13) or of a myeloproliferative/myelodysplastic disorder (n=2), as defined by the WHO criteria (Jaffe E S, et al. World Health Organization Classification of Tumors. Pathology and Genetics of Tumors of Haematopoietic and Lymphoid Tissues. Lyon: IARC Press; 2001), were collected with informed consent (patient characteristics are outlined in Table 1). All samples were reviewed and classified by the hematopathology service at the Hospital of the University of Pennsylvania. The control group consisted of 16 samples selected from excess material submitted to the hematology laboratory for routine CBCs from patients without MDS. For the validation study, blinded samples were provided from de-identified samples (n=31) of patients with cytopenias and/or hematologic dysplasia noted on the peripheral blood smear. For the validation study, the hematology laboratory provided a blinded series of 31 patients, with cytopenias and/or dysplasias.

Sample Preparation

All samples were collected in EDTA-containing tubes and processed within 24 hours of collection. Peripheral blood samples were subjected to whole blood red blood cell lysis with 1× ammonium chloride ($NH_4Cl$ concentration of 0.15 mol/ml) lysing solution for 10 minutes at room temperature. After lysis, the cells were washed twice with PBS and resuspended in staining buffer (PBS with 0.5% Bovine Serum Albumin). The peripheral blood leukocytes were then stained according to manufacturers recomnmendations with a panel of antibodies, directly conjugated to fluorochromes, specific for antigens expressed at various stages of normal and abnormal myeloid differentiation (Kussick S J and Wood B L. Archives of Pathology & Laboratory Medicine 2003; 127(9): 1140-7) or against antigens that have been reported altered in MDS (Table 2). All antibodies were obtained from BD Biosciences (San Jose, Calif.) with the exception of anti-CD64-PE (Caltag Laboratories, Burlingame, Calif.) and anti-CD116-PE (Immunotech, Marseille, France). All antibodies used are routinely quality controlled and evaluated for appropriate concentration by the clinical flow cytometry laboratory of the Hospital of the University of Pennsylvania Concentrations used have been found to be greater than or equal to saturating levels. After staining, samples were washed ×2 with staining buffer, resuspended in staining buffer and analyzed immediately.

Flow Cytometric Analysis

Data were acquired on a FACSCalibur (BD Biosciences) calibrated daily using Spherotech 8 peak beads (Spherotech, Inc., Libertyville, Ill.) according to manufacturer's instructions for daily instrument quality control. Compensation was adjusted using cells stained with CD8-FITC, CD8-PE, CD8-PerCP and CD8-APC (all directly conjugated and processed in an identical fashion to the test samples). Data was analyzed using Flow Jo Software (Treestar, San Carlos, Calif.). A four-color panel was used, with FITC, PE, and PerCP excited by the 488 nm argon laser and detected in FL1, FL2, and FL3 respectively and APC excited by the 635 nm red diode laser and detected in FL4. In each preparation, a minimum of 10,000 total events was collected. CD45 PerCP was included in each tube to allow identification of PMNs using CD45 versus side scatter (SSC) gating (Stelzer G T, et al., Annals of the N Y Academy of Science 1993; 677; 265-280) (FIG. 1). Geometric mean fluorescent intensity (G-MFI) was derived for the auto fluorescence control and for each antibody. The G-MFI for each antibody was then corrected for the autofluorescence, (Test G-MFI—Auto G-MFI)/(Auto G-MFI), to generate the corrected G-MFI (adapted from method used by Maynadie et al., Blood 2002; 100(7):2349-56). To assess PMN SSC, the corrected PMN SSC was quantitatively express as (mean PMN SSC)/(mean Lymphocyte SSC), since myeloid cell granularity can be represented as the difference in lymphocyte and myeloid granularity.

Statistical Analysis

The Mann-Whitney U test was used to assess statistical differences between groups. All statistical calculations were performed using Analyze-it for Microsoft Excel, Leeds, UK.

Example 1

Alterations in Side Scatter and Immunophenotypic Patterns in Peripheral Blood Neutrophils From MDS Patients Patient samples evaluated were as listed in Table 1.

TABLE 1

Clinical parameters and MDS scores

| Sample | Diagnosis 1 | Age | Sex | WBC | Hemoglobin | Platelets | ANC | Cytogenetics | Marrow Blasts | IPSS | MDS Score |
|---|---|---|---|---|---|---|---|---|---|---|---|
| 1 | MDS-U | 78 | M | 4.9 | 6.1 | 39 | 3185 | Normal | <5% | 0.5 | 7 |
| 2 | RCMD | 71 | F | 3.1 | 7.6 | 64 | 2511 | Normal | <2 | 0.5 | 5 |
| 3 | RA | 50 | F | 7.3 | 9.5 | 148 | 7400 | Normal | 3 | 0 | 4 |
| 4 | RAEB-2 | 59 | F | 8.2 | 8.6 | 26 | 4838 | Complex 2 | 16 | 3 | 8 |
| 5 | RARS | 58 | F | 4.3 | 7.8 | 341 | 2900 | Normal | 0.3 | 0 | 4 |
| 6 | RCMD | 61 | M | 2.3 | 7.1 | 46 | 1432 | Normal | 2 | 0.5 | 3 |
| 7 | RCMD | 79 | M | 1.9 | 6.9 | 189 | 1254 | Normal | 2 | 0.5 | 2 |
| 8 | RA | 79 | M | 1.7 | 9.4 | 68 | 560 | Normal | 1 | 0.5 | 7 |
| 9 | RAEB-2 | 73 | M | 2.1 | 11.1 | 58 | 672 | Normal 3 | 18 | 2 | 0 |
| 10 | RAEB-1 | 77 | M | 2.5 | 8.5 | 23 | 1350 | Normal | 6 | 1 | 3 |
| 11 | CMML-1 | 83 | M | 7.3 | 11.4 | 175 | 3796 | NA 4 | 2 | NA 5 | 4 |
| 12 | CMML-2 | 66 | M | 5 | 11.9 | 139 | 1443 | Normal | 15 | 1.5 | 6 |
| 13 | RCMD | 63 | M | 12.5 | 13.6 | 46 | 10000 | Normal | 4 | 0 | 3 |
| 14 | RCMD | 47 | F | 17.8 | 9.4 | 29 | 11104 | I (17)(q10) | 4 | 1 | 4 |
| 15 | RCMD | 75 | M | 3.7 | 8.9 | 185 | 998 | del (5)(q15q35) | 1 | 1.5 | 4 |
| † | Mean | 67.93 | | 5.64 | 9.19 | 105.07 | | | | | |
| † | Standard Dev | 11.20 | | 4.50 | 2.07 | 89.59 | | | | | |
| Control (N = 16) | | † | † | † | † | † | † | † | | † | † |
| | Mean | 54.13 | | 7.58 | 11.52 | 295.81 | | | | | |
| | Standard Dev | 18.01 | | 2.77 | 2.19 | 104.63 | | | | | |

1 WHO classification: MDS-U = MDS-unclassified (case 1 = MDS with fibrosis); RCMD = refractory cytopenia with multilineage dysplasia; RA = refractory anemia; RAEB = refractory anemia with excess blasts; RARS = refractory anemia with ringed sideroblasts; CMML = chronic myelomonocylic leukemia; aCML = atypical chronic myelogenous leukemia
2 43-45, X, del(X)(p22), del(1)(p32p36.3), add(3)(?q21).–5, add(5)(p13), –7, –10, del(11)(q23), del(12) (p13)–13, –19, –20, –22, +2-4mar[cp25]
3 2/65 cells with del(7)(q22q32)
4 NA = not available
5 Calculation of IPSS requires cytogenetics In preliminary studies, patient samples as outlined in Table 1 were subjected to probing by an intensive panel, and samples were evaluated, in terms of monocyte and blast (identified by CD45/SSC gating) as well as neutrophil (PMN) characteristics, however changes in the PMNs were found to be most informative (Table 2).

TABLE 2

Peripheral Blood MDS Antibody Panel

| | Flourochrome | | | |
|---|---|---|---|---|
| Sample | FITC | PE | PERCP | APC |
| 1 | | | CD45 | |
| 2 | CD71 | CD10 | CD45 | CD32 |
| 3 | CD16 | CD116 | CD45 | CD13 |
| 4 | CD18 | CD11a | CD45 | CD11b |
| 5 | CD59 | CD55 | CD45 | CD56 |

TABLE 2-continued

Peripheral Blood MDS Antibody Panel

| | Flourochrome | | | |
|---|---|---|---|---|
| Sample | FITC | PE | PERCP | APC |
| 6 | CD90 | CD117 | CD45 | CD34 |
| 7 | CD43 | CD64 | CD45 | HLA DR |
| 8 | CD66 | CD44 | CD45 | CD33 |

[a] Four color panels were devised using FITC (fluorescein isothiocyanate), PE (phycoerythrin), PerCP (peridin chlorophyll protein), and APC (allophycocanin).

Figure 2:
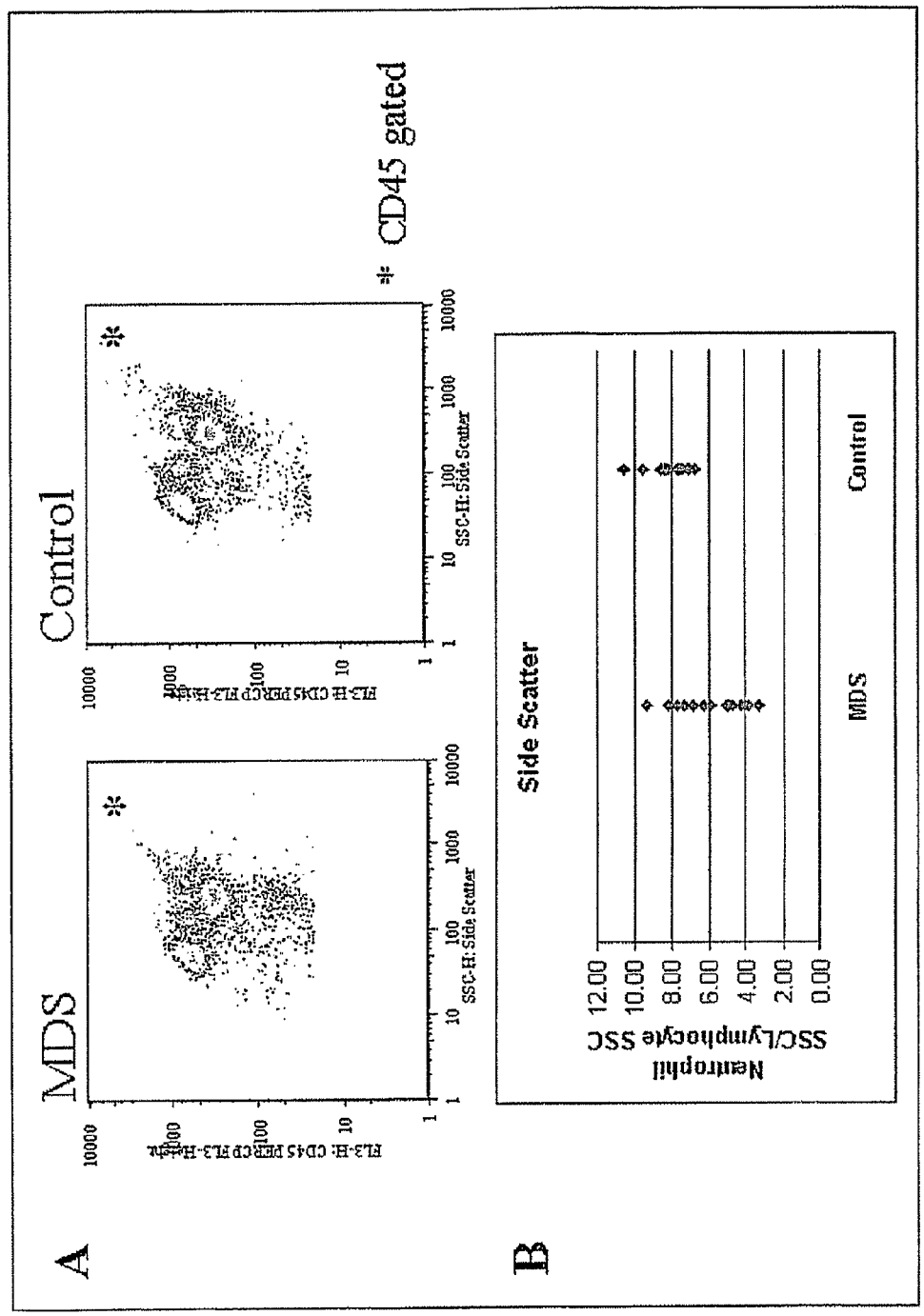
FIG. 2 demonstrates side scatter abnormalities observed in flow cytometric analysis of samples from subjects with MDS. A) CD45 versus side scatter plot of a representative MDS and control sample. B) MDS PMNs have a significantly lower side scatter than that of normal controls (P=0.001)
Figure 3:
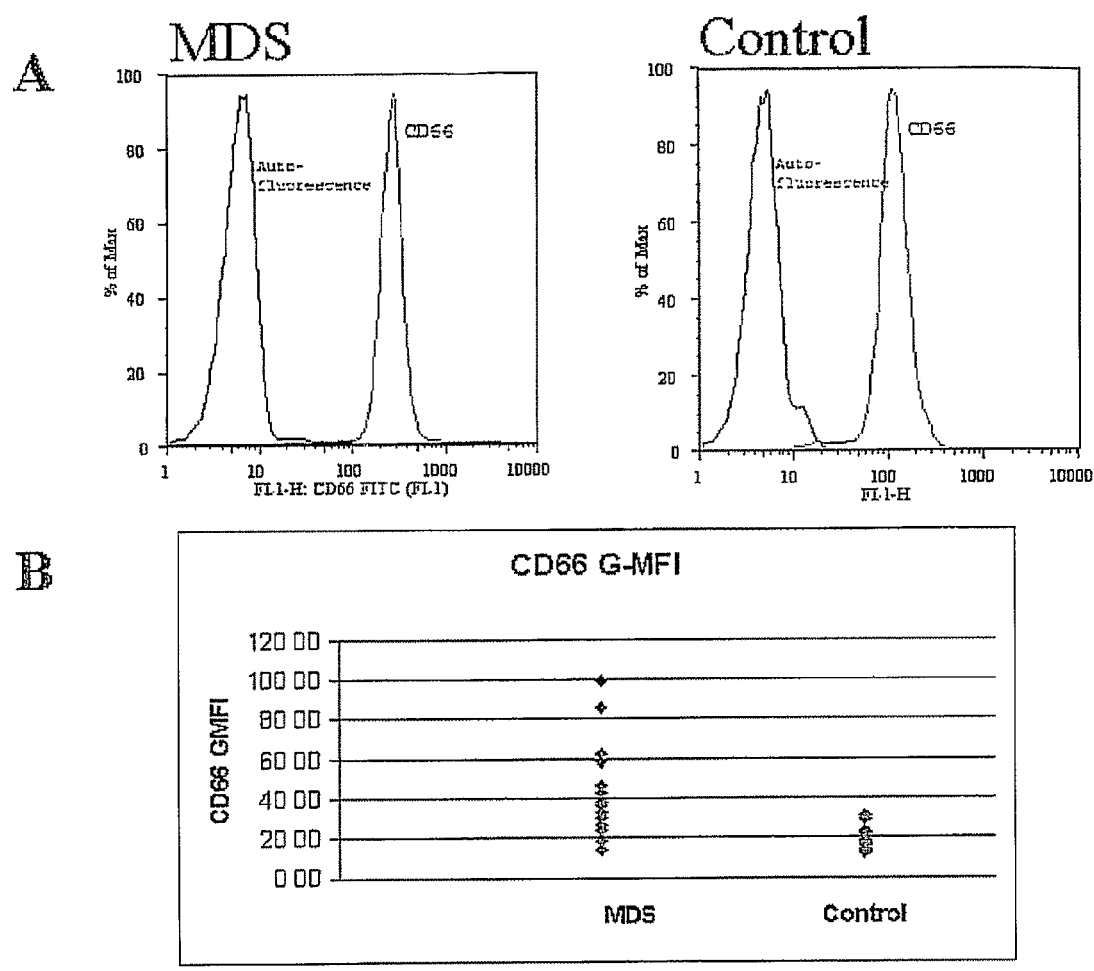
FIG. 3 demonstrates increased CD66 expression on PMNs obtained from peripheral blood of MDS patients versus controls. A) CD66 and autofluorescence is demonstrated for a representative patient with MDS and for a control sample. B. CD66 expression was significantly higher for MDS samples than controls (p=0.0003).
Figure 4:
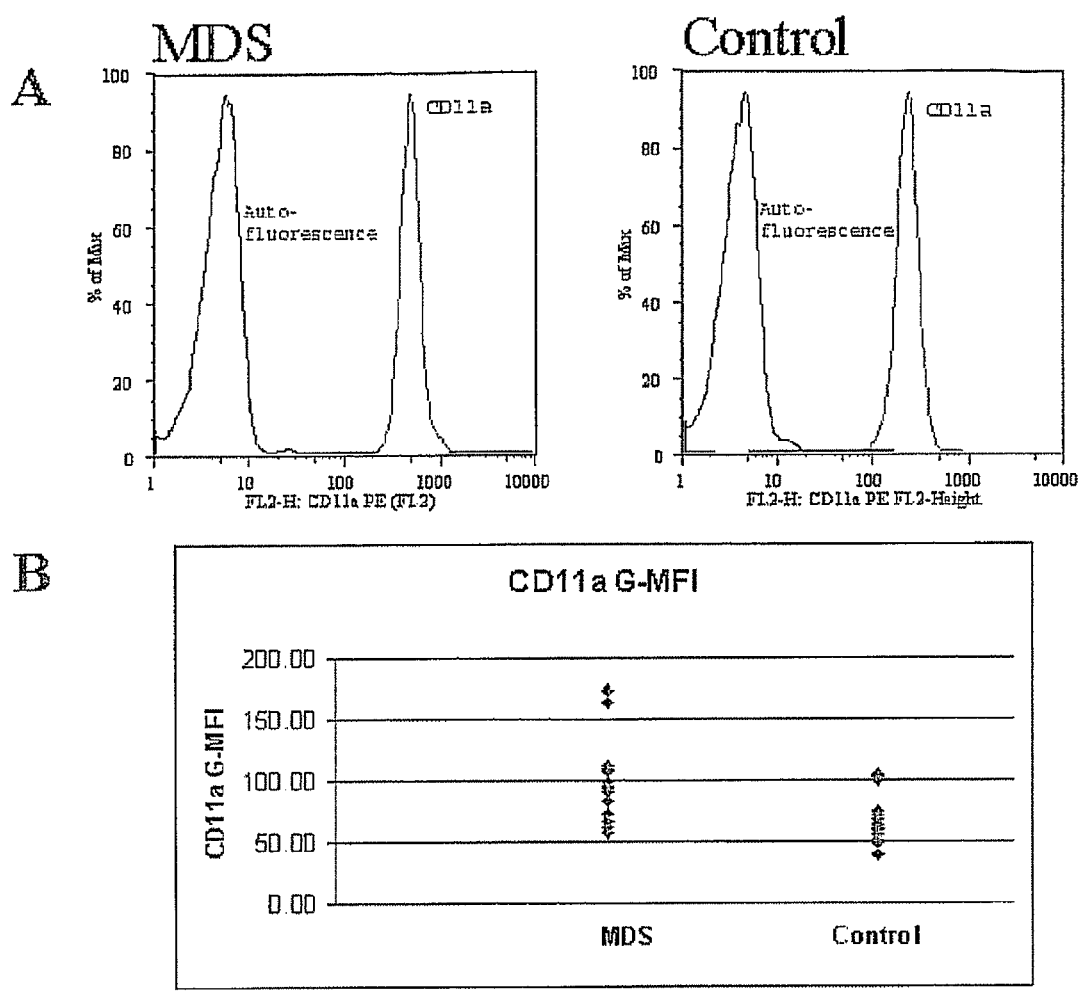
FIG. 4 demonstrates increased CD11a expression on PMNs from MDS patients as opposed to controls. A) CD11a and autofluorescence is demonstrated for a representative patient with MDS and for a control sample. B. CD11a expression was significantly higher in MDS samples in comparison to controls (p=0.008).

PMNs have been described to be immunophenotypically, morphologically and functionally abnormal in patients with MDS. Using an extensive panel of immunophenotypic markers, chosen as outlined above, several significant, quantifiable alterations in PMNs were identified in samples from MDS patients. Peripheral blood granulocytes demonstrated a significant decrease in side scatter capability, as compared to controls, reflecting hypogranularity (corrected SSC of 5.81+/−1.73 versus 7.94+/−1.01, p=0.001) (FIG. 2). In addition, PMNs from MDS patients had significantly higher expression of CD66 (corrected CD66 G-MFI 42.35+/−24.75 versus 18.78+/−5.56, p=0.0003) and CD11a (corrected CD11a G-MFI 98.66+/−33.02 versus 69.39+/−19.03, p=0.008) (FIGS. 3 and 4) as compared to controls. Variable abnormalities of CD10 [previously demonstrated in bone marrow granulocytes] and CD116 were noted in some samples. Specifically, one patient demonstrated marked loss of CD10, one patient demonstrated CD116 expression >2SD above mean value for controls, and 2 patients demonstrated CD116 expression <2 SD below the mean value for controls.

Example 2

Development of a Peripheral Blood MDS Score

As MDS are a heterogeneous group of diseases it is unlikely that any parameter taken in isolation would allow discrimination of all patients with MDS. Thus, a scoring system was devised as a method to associate the heterogeneous immunophenotypic data into a format, which is more readily interpreted.

Because phenotypic changes were observable in peripheral blood-derived PMN samples from MDS patients, it was of interest to determine whether a scoring system, based only on peripheral blood neutrophils could be developed.

To create the score statistically significant differences (SSC, CD11a expression, CD66 expression) were assigned 1 point for variations obtained which exhibited from 1-2 standard deviations (SD) from the control mean value, and 2 points for variations obtained which exhibited more than 2 standard deviations (SD) from the control mean value. In addition, points were assigned for other described abnormalities such as loss of CD10 or abnormal CD116 expression.

Figure 5:
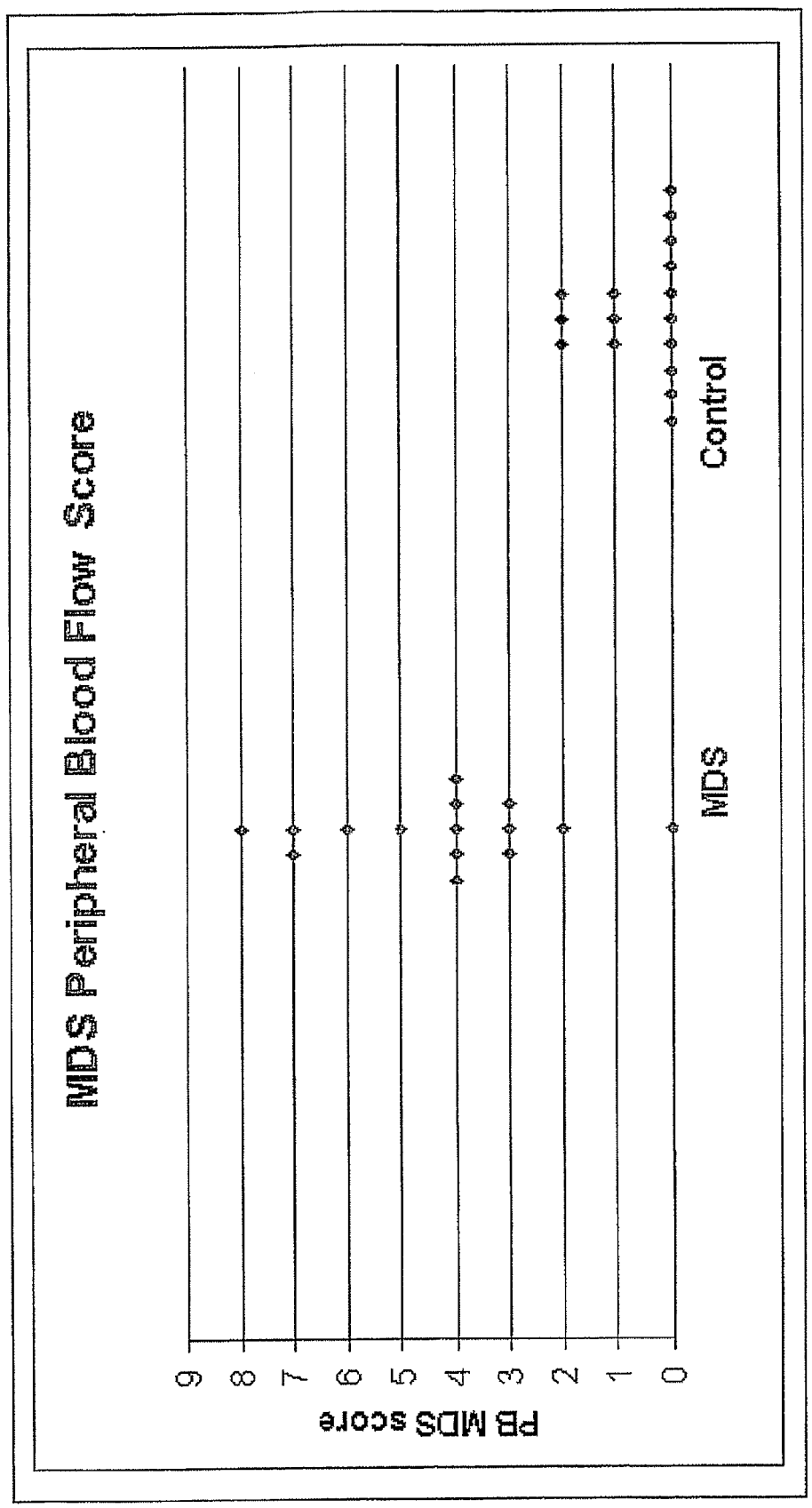
FIG. 5 demonstrates the development of the PB MDS score. The PB MDS score was calculated by combining the noted abnormalities identified in patients with MDS as described. As illustrated, the PB MDS score was significantly higher in patients with MDS than in normal controls (p<0.0001).

Because abnormalities in CD10 and CD116 were rare in the test set, 2 points were given for either loss of CD10 or abnormal CD116 expression (2 SD either above or below the mean of normal). The sum of points for each sample was defined as the PB MDS score. The PB MDS score was significantly higher in patients with MDS, as compared to controls (4.27+/−2.09 versus 0.56+/−0.81, p<0.0001) (FIG. 5).

Example 3

Validation of the Peripheral Blood MDS Score

In order to validate the accuracy of the PB MDS score, the diagnostic approach was applied to a "blinded" series of samples obtained from 31 patients, which suffered from cytopenias and/or hematopoietic dysplasia. After completion of the scoring, diagnoses were "unblinded", and samples were evaluated in terms of WHO criteria, where it was found that 11 samples were obtained from patients with a confirmed diagnosis of MDS (using the WHO criteria) while the remaining 20 samples were obtained from patients who did not have MDS (diagnoses included anemia of chronic disease, iron deficiency anemia, consumptive thrombocytopenias, etc.) (Table 3).

TABLE 3

Validation of the PB MDS Score

| Sample | Diagnosis | MDS Score |
|---|---|---|
| MDS Patients: | | |
| 1 | RAEB-1 | 1 |
| 2 | MDS with fibrosis | 3 |
| 3 | RCMD | 3 |
| 4 | RAEB-2 | 4 |
| 5 | RCMD with myeloproliferative features | 4 |
| 6 | MDS-U | 4 |
| 7 | RA | 5 |
| 8 | RCMD | 5 |
| 9 | RCMD | 5 |

TABLE 3-continued

Validation of the PB MDS Score

| Sample | Diagnosis | MDS Score |
|---|---|---|
| 10 | MDS-U, recurrent post transplant | 6 |
| 11 | RCMD | 8 |
| Mean | | 4.36 |
| Controls: | | |
| 1 | AML* | 0 |
| 2 | Iron Deficiency Anemia | 0 |
| 3 | Anemia of Chronic disease | 0 |
| 4 | Anemia of Chronic disease | 1 |
| 5 | Anemia of Unknown Etiology | 1 |
| 6 | Anemia of Unknown Etiology | 1 |
| 7 | Anemia of Chronic disease | 2 |
| 8 | Anemia of Unknown Etiology | 2 |
| 9 | Anemia of Chronic disease | 2 |
| 10 | Chronic Idiopathic Myelofibrosis | 2 |
| 11 | AML* | 2 |
| 12 | Anemia of Chronic disease | 2 |
| 13 | Anemia of Chronic disease | 3 |
| 14 | Anemia of Chronic disease | 3 |
| 15 | Chemotherapy for carcinoma | 3 |
| 16 | Thrombocytopenia of Unknown Etiology | 3 |
| 17 | Chronic Idiopathic Myelofibrosis | 3 |
| 18 | Anemia of Chronic disease | 3 |
| 19 | Anemia of Chronic disease | 4 |
| 20 | Chronic Lymphocytic Leukemia | 4 |
| Mean | | 2.05 |

Each Control patient had at least one cytopenia, none with documented MDS;
*AML, acute myelogenous leukemia.

Figure 6:
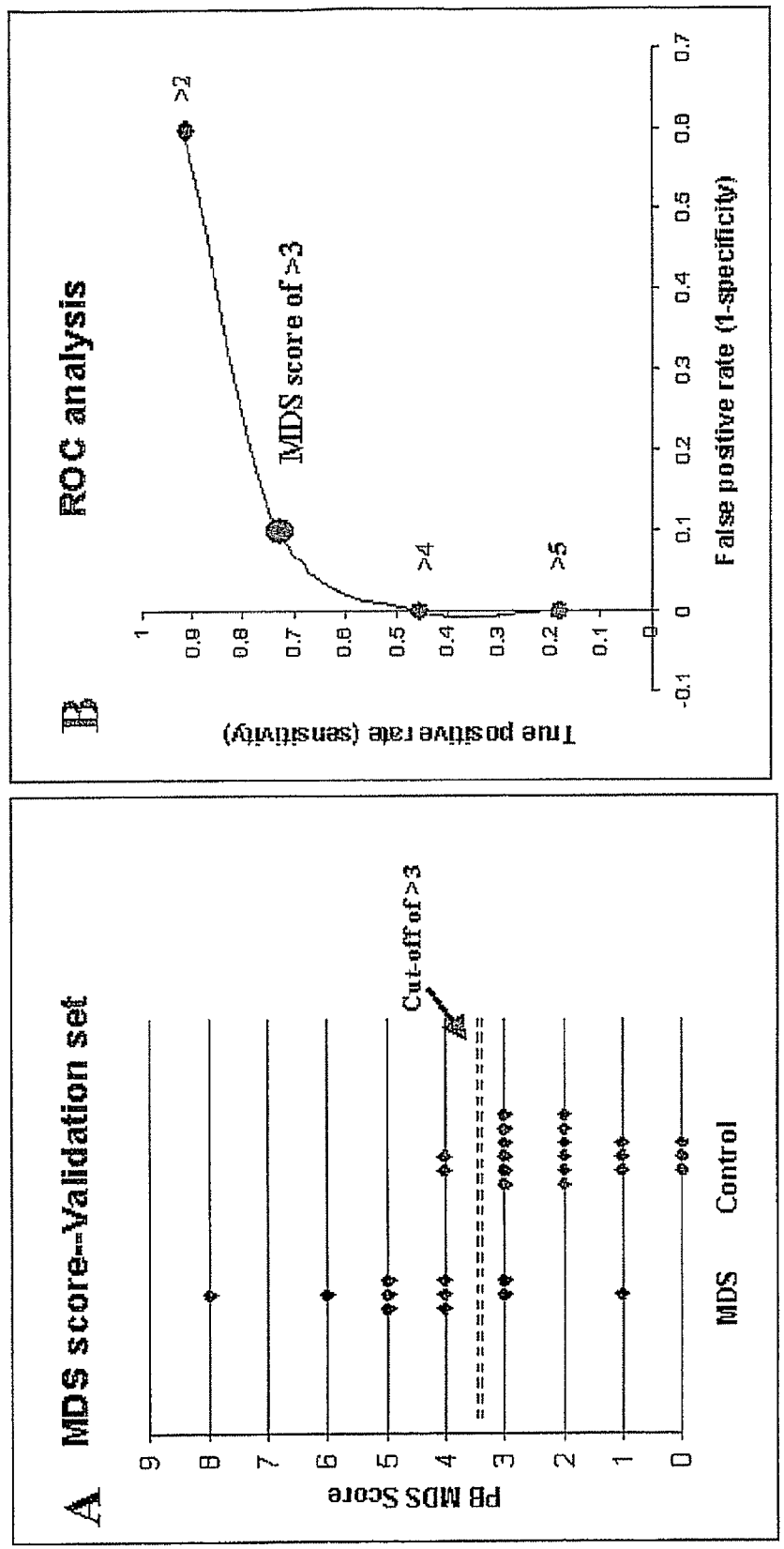
FIG. 6 demonstrates the validation of the PB MDS Score. The MDS score was validated in a set of unknown samples taken from patients with cytopenias and/or dysplasia on peripheral blood smear. A) In the validation set, patients with MDS have a higher PB MDS score than those without MDS (p=0.0005). B) A receiver-operating curve analysis demonstrates that using a cut-off of >3 to identify patients with MDS minimizes false positives and false negatives in the validation set.

Scores assigned for samples obtained from patients with MDS (as diagnosed using WHO criteria) were significantly higher than those assigned for controls (4.36+/−1.80 versus 2.05+/−1.23 for patients without MDS, p=0.0005) (FIG. 6a), thus validating the MDS scoring procedure.

A receiver operating curve analysis performed on the validation set (FIG. 6b) illustrated that a cut-off of >3 maximizes the sensitivity and specificity of the peripheral blood MDS score. Using a cut-off point of >3 to define MDS, 3 patients with MDS were misclassified and 2 controls were misclassified. Using this cut-off, in the validation set, the MDS score performed with a sensitivity of 73% and a specificity of 90%.

Thus, a scoring algorithm, which evaluated side scatter and immnunophenotypic data, derived from a multiparameter flow cytometric analysis of peripheral blood PMNs accurately distinguished patients with MDS from controls. The multiparameter analysis entailed analysis of only 5 parameters of a subset of peripheral blood cells, yet the scoring system integrates information regarding the heterogeneity of phenotypic changes observed in MDS. The algorithm or MDS score is therefore a useful adjunct in the diagnosis of MDS, which is at least as sensitive as existing testing methods, and more specific for the identification of patients with MDS.

Example 4

Calculation of the Peripheral Blood MDS Score

Specimen Processing

Whole blood collected in EDTA is subjected to $NH_4Cl$ red blood cell lysis. Lysed cells are washed 2× with PBS. Cells are washed and resuspended in staining buffer (PBS with 0.5% BSA).

Antibody Panel and Staining

Cells are incubated with antibodies directly conjugated to fluorochromes (FITC, PE or PerCP) in the combinations demonstrated in Table 4 according to manufacturers recommendations.

TABLE 4

Antibody panel

| Tube | FITC (FL1) | PE (FL2) | PERCP (FL3) |
|---|---|---|---|
| 1 | Autofluorescence | Autofluorescence | CD45 |
| 2 | CD66 | | CD45 |
| 3 | | CD11a | CD45 |
| 4 | | CD116 | CD45 |
| 5 | | CD10 | CD45 |

FITC = fluorescein isothiocyanate
PE = phycoreythrin
PerCP = peridinin chlorophyll protein Analysis:

Data were acquired on a FACSCalibur (BD Biosciences, San Jose, Calif.) and analyzed using Flow Jo Software (Treestar, San Carlos, Calif.). In each preparation, 20,000 total events were collected.

Figure 7:
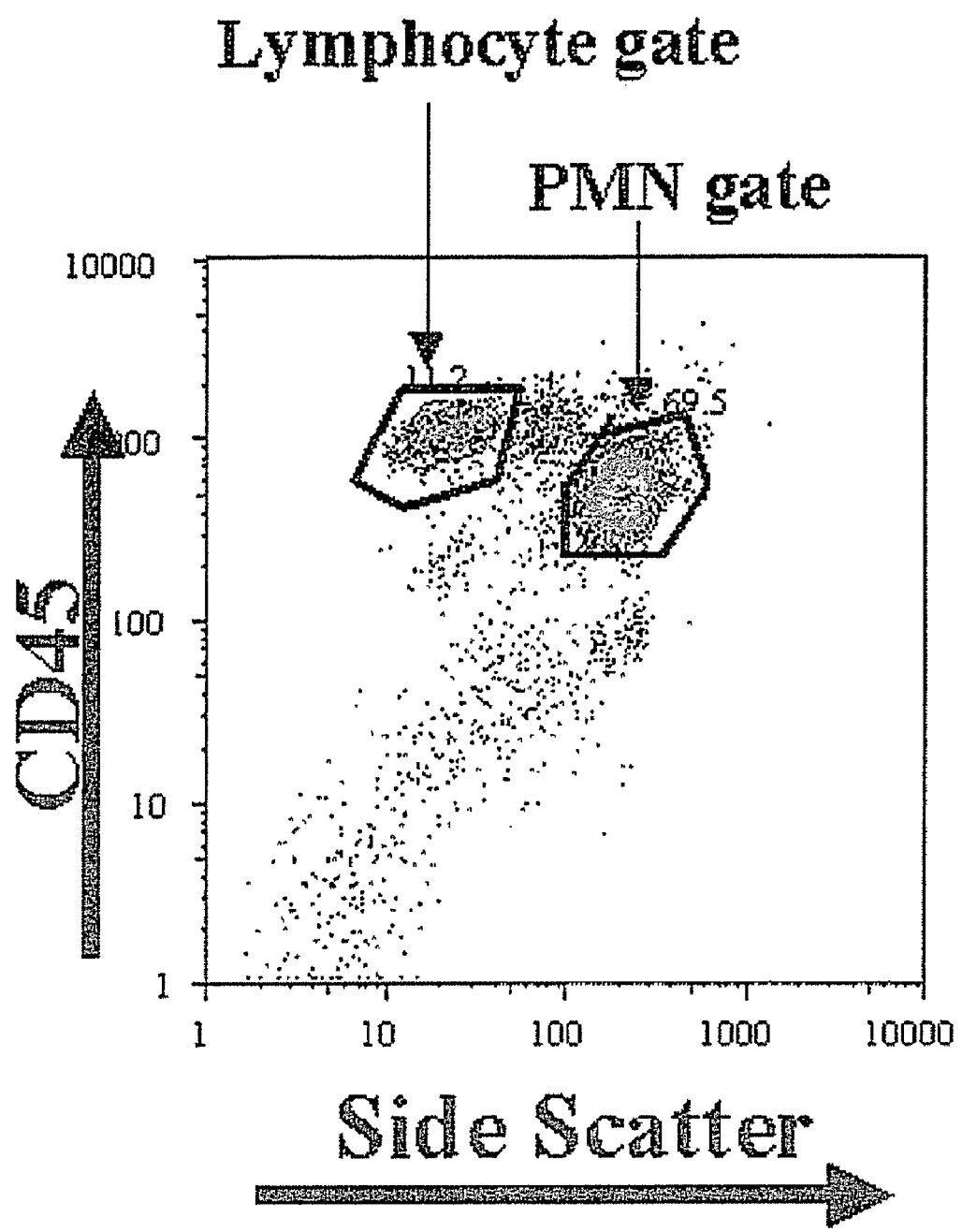
FIG. 7 shows the gating strategy and calculation of corrected side scatter. CD45 versus side scatter gating was used to identify lymphocytes and PMN in PB samples. The corrected PMN side scatter (SSC) was defined (as the mean PMN SSC/mean Lymphocyte SSC).
Figure 8:
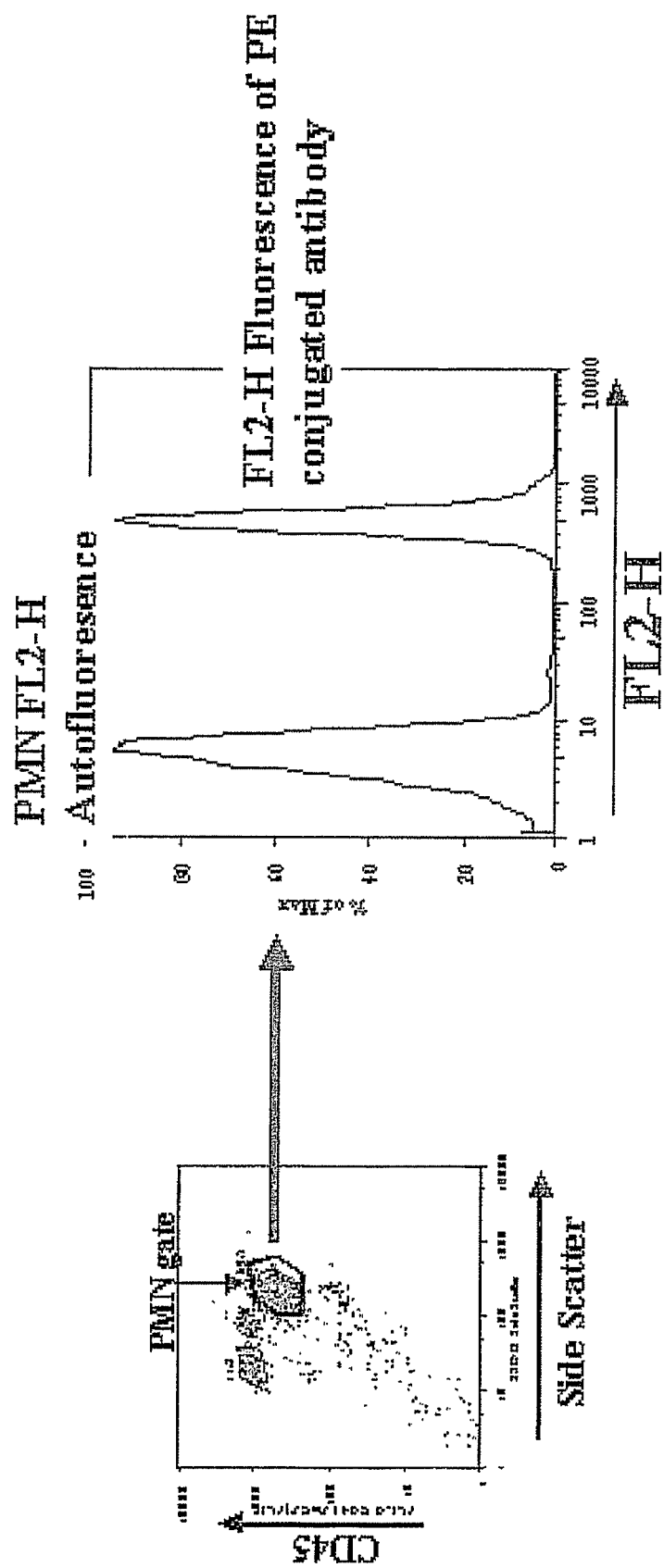
FIG. 8 shows the calculation of corrected antigen G-MFI. Using tube 1 stained with only CD45 PERCP, the PMN autofluorescence was determined for the FL1 and FL2 channels. Then, for each antigen, the PMN G-MFI was calculated. The corrected G-MFI was defined as the [(test antigen Q-MFI-autofluorescence G-MFI)/autofluorescence G-MFI].

The corrected PMN side scatter and geometric fluorescent intensity for each immunophenotypic marker were calculated as outlined in FIGS. 7 and 8 in a normal control population to establish the normal reference ranges. Corrected PMN side scatter and G-MFI values were calculated for PB samples from patients with MDS. The PB MDS score was calculated as outlined in Table 5.

TABLE 5

Calculation of PB MDS score

| | 0 points | 1 point | 2 points |
|---|---|---|---|
| SSC | Within 1 SD of mean of normals | 1-2 SD from the mean of normals | >2 SD from the mean of normals |
| CD66 | | | |
| CD11a | | | |
| CD116 | | | |
| CD10 | | | Loss of expression |

Sum of points = PB MDS SCORE

Results

In a validation set including patients with cytopenias and/or morphologic dysplasia, a PB MDS score 3 or greater identifies patients with MDS with a sensitivity of 73% and a specificity of 90%.

Example 5

Flow Cytometric Analysis of Peripheral Blood Neutrophils: A Simple, Objective, Independent and Potentially Clinically-useful Assay to Facilitate the Diagnosis of Myelodysplastic Syndromes Materials and Methods Cytogenetic Analysis Cytogenetic analysis was performed on unstimulated 24-hour cultures of bone marrow using standard techniques.

Results

The distribution of WHO subtypes, hematologic parameters, cytogenetic results, IPSS and FCM MDS scores, are detailed in Table 6.

TABLE 6

Clinical parameters and MDS scores.

| Case | Age | SEX | Diagnosis[1] | Hem. | Platelets | WBC | ANC | Cytopenias | Marrow Blasts | Cytogenetics | IPSS[2] | MDS score |
|---|---|---|---|---|---|---|---|---|---|---|---|---|
| 1 | 78 | M | MDS-U | 6.1 | 39 | 4.9 | 3185 | 2 | <5 | Normal | 0.5 | 7 |
| 2 | 71 | F | RCMD | 7.6 | 64 | 3.1 | 2511 | 2 | 1 | Normal | 0.5 | 5 |
| 3 | 50 | F | RA | 9.5 | 148 | 7.3 | 7400 | 1 | 3 | Normal | 0 | 4 |
| 4 | 59 | F | RAEB-2 | 8.6 | 26 | 8.2 | 4838 | 2 | 16 | Complex[3] | 3 | 8 |
| 5 | 58 | F | RARS | 7.8 | 341 | 4.3 | 2900 | 1 | 0.3 | Normal | 0 | 4 |
| 6 | 61 | M | RCMD | 7.1 | 46 | 2.3 | 1432 | 3 | 2 | Normal | 0.5 | 3 |
| 7 | 79 | M | RCMD | 6.9 | 189 | 1.9 | 1254 | 2 | 2 | Normal | 0.5 | 2 |
| 8 | 79 | M | RA | 9.4 | 68 | 1.7 | 560 | 3 | 1 | Normal | 1.5 | 7 |
| 9 | 73 | M | RAEB-2 | 11.1 | 58 | 2.1 | 672 | 2 | 18 | Normal[4] | 2 | 0 |
| 10 | 77 | M | RAEB-1 | 8.5 | 23 | 2.5 | 1350 | 3 | 6 | Normal | 1 | 3 |
| 11 | 83 | M | CMML-1 | 11.4 | 175 | 7.3 | 3796 | 0 | 2 | NA[5] | NA[9] | 4 |
| 12 | 66 | M | CMML-2 | 11.9 | 139 | 5 | 1443 | 1 | 15 | Normal | 1.5 | 6 |
| 13 | 63 | M | RCMD | 13.6 | 46 | 12.5 | 10000 | 1 | 4 | Normal | 0 | 3 |
| 14 | 47 | F | RCMD | 9.4 | 29 | 17.8 | 11104 | 2 | 4 | i(17)(q10) | 1 | 4 |
| 15 | 75 | M | RCMD | 8.9 | 185 | 3.7 | 998 | 2 | 1 | del (5) (q15q35) | 1.5 | 4 |
| 16 | 57 | F | MDS-U | 8.1 | 44 | 12.6 | 6300 | 2 | 8 | Complex[6] | 2 | 6 |
| 17 | 55 | M | RCMD | 9.6 | 19 | 7.1 | 3519 | 2 | 15 | Normal | 2 | 8 |
| 18 | 65 | M | RAEB-1 | 13.7 | 8 | 13.3 | 7800 | 1 | 8 | Normal | 0.5 | 1 |
| 19 | 19 | M | RAEB-2 | 8.2 | 26 | 20.4 | 14848 | 2 | 11 | Normal | 2 | 4 |
| 20 | 72 | M | RCMD | 9.3 | 22 | 4.3 | 1848 | 2 | 1 | i(17) (q10), +13 | 1 | 5 |
| 21 | 40 | F | aCML | 7.2 | 43 | 195 | 68444 | 2 | 2 | Normal | 0.5 | 4 |
| 22 | 72 | M | RCMD | 9.2 | 277 | 4.8 | 4080 | 1 | 0 | Complex[7] | 0.5 | 5 |
| 23 | 75 | M | MDS-U | 9.1 | 18 | 1.1 | 418 | 3 | <5 | NA[5] | NA[9] | 3 |
| 24 | 54 | M | RCMD | 13.2 | 115 | 6 | 3000 | 0 | 1 | Normal | 0 | 3 |
| 25 | 84 | F | RCMD-RS | 8.3 | 334 | 7.2 | 5652 | 1 | 0 | Complex[8] | 1 | 2 |

TABLE 6-continued

Clinical parameters and MDS scores.

| Case | Age | SEX | Diagnosis[1] | Hem. | Platelets | WBC | ANC | Cyto-penias | Marrow Blasts | Cytogenetics | IPSS[2] | MDS score |
|---|---|---|---|---|---|---|---|---|---|---|---|---|
| Mean | 64.48 | | | 9.35 | 99.28 | 14.26 | 6774.1 | | | | 1.00 | 4.20 |
| SD | 15.09 | | | 2.07 | 99.74 | 37.99 | | | | | 0.81 | 2.02 |

[1]WHO classification: MDS-U = MDS-unclassified (cases 1 and 23 = with fibrosis, case 16 = MDS following bone marrow transplant for secondary AML); RCMD = refractory cytopenia with multilineage dysplasia; RA = refractory anemia; RAEB = refractory anemia with excess blasts; RARS = refractory anemia with ringed sideroblasts; CMML = chronic myelomonocytic leukemia; aCML = atypical chronic myelogenous leukemia; RCMD-RS = refractory cytopenia with multilineage dysplasia and ringed sideroblasts.
[2]IPSS = International Prognostic Scoring System score, calculated as previously described (2).
[3]43-45, X, del(X)(p22), del(1)(p32p36.3), add(3)(?q21), −5, add(5)(p13), −7, −10, del(11)(q23), del(12) (p13)−13, −19, −20, −22, +2−4mar[cp25]
[4]2/65 cells with del(7)(q22q32)
[5]NA = not available
[6]t(1; 2), −5, der(7), t(7; 12), −12, −16, del(19q13.3)
[7]46XY, t(2; 11)(p21q23), del; (5)(q15; q33)
[8]46XX, del(12)(p11.2p13), del(20)(q11.2q13.3) in 11 cells/45, XX, −7, del(20)(q11.2q13.3) in 15 cells.
[9]IPSS cannot be calculated without cytogenetic data A PB MDS score of greater than 3 was determined in previous examples to distinguish MDS patients from controls with a sensitivity of 73% and a specificity of 90%. Using this cut-off, 16/25 (64%) patients in this series have a positive score. In isolation, the score's role may appear to be modest; however, in the context of a disease in which the "gold standard" of cytogenetics may be abnormal in only 50% of cases, it provides a useful and quantifiable, complementary diagnostic tool. Strikingly, 9/16 cases with normal cytogenetics had positive PB MDS scores indicating that FCM may be a much more sensitive marker of MDS than cytogenetics.

There was no significant correlation between the PB MDS score and peripheral blood counts or marrow blast count (p=0.55-0.70). PB MDS scores of patients with cytogenetic abnormalities were not significantly different from patients without cytogenetic abnormalities (p=0.54). Although the numbers are small, there was no correlation with IPSS or WHO categorization. Thus, these preliminary data suggest that the PB MDS score may vary independently of parameters known to be diagnostically and prognostically useful in the evaluation of MDS.

An important difference in this FCM assay, compared with those developed by others, is its unexpected simplicity, requiring analysis of only five parameters. The complexity of some previously described assays is such that as many as twenty parameters may need to be assessed. Additionally, this assay is performed in peripheral blood making it relatively non-invasive. Accordingly, this assay may be easier to implement in a clinical flow cytometry laboratory.

PB MDS score may therefore have valuable diagnostic applications in this sometimes enigmatic group of diseases, since it is (1) positive in patients with normal cytogenetics, (2) simple and (3) non-invasive.

What is claimed is:

1. A method of for diagnosing a subject with a myelodysplastic syndrome (MDS) in a subject, comprising analyzing predictive parameters in a blood sample of said subject; assigning a numerical value corresponding to a measure of each of said predictive parameters; comparing the said value to a value obtained for said predictive parameters from a control group; and assigning a numerical score reflecting the variance between the mean values obtained for said predictive parameters in said subject and that obtained for the same predictive parameters in said control group wherein said predictive parameters comprise: a measure of polymorphic neutrophil (PMN) granularity and expression of CD66, CD11a, CD10, and CD116 in cells of said blood sample, and wherein said numerical score provides indication of the presence or absence of said syndrome in said subject.

2. The method of claim 1, wherein said method employs flow cytometry.

3. The method of claim 2, wherein said predictive parameters further comprises side scatter capability.

4. The method of claim 3, wherein said cell granularity is assessed by evaluating CD45 expression as a function of side scatter of said PMN.

5. The method of claim 1, further comprising the step of lysing red blood cells from said blood sample.

6. The method of claim 1, wherein said blood sample is enriched for leukocytes.

7. The method of claim 1, wherein said blood sample is enriched for neutrophils.

8. The method of claim 1, wherein said control sample is selected from a subject, or pool of subjects without MDS.

9. The method of claim 8, wherein a significant difference between the value of each parameter in said subject and said control group of less than 2 standard deviations (SD) is scored as 1, and a significant difference between said subject and said control group of greater than 2 SD is scored as 2, wherein a combined score of about 2 or greater indicates that said subject suffers from MDS.

10. The method of claim 1, wherein said control sample is selected from a subject, or pool of subjects with MDS.

11. The method of claim 10, wherein a significant difference between the value of each parameter in said subject and said control group of less than 2 standard deviations (SD) is scored as 1, and a significant difference between said subject and said control group of greater than 2 SD is scored as 2, wherein a combined score of about 2 or greater indicates that said subject does not suffer from MDS.

12. The method of claim 1, wherein said myelodysplastic syndrome (MDS) is refractory cytopenia with multilineage dysplasia (RCMD) refractory anaemia (RA), acquired idiopathic sideroblastic anemia (AISA), refractory anaemia with ring sideroblasts (RARS), refractory anaemia with excess blasts (RAEB), refractory anaemia with excess blasts in transformation (RAEB-t), chronic myelomonocytic leukaemia (CMML), atypical chronic myelogenous leukemia (aCML), 5q syndrome diseases, which are erythroid dysplasia, thrombocytosis, or hypolobated micromegakaryocytic hyperplasia, or a combination thereof.

13. A kit for carrying out the method for diagnosis of a myelodysplastic syndrome (MDS) of claim 1, the kit comprising antibodies, antibody fragments or molecular beacons that are specifically reactive to CD66, CD11a, CD10, CD116, and CD45 and instructions for diagnosis of said syndrome using antibodies, antibody fragments or molecular beacons.

14. The kit of claim 13, wherein one or more of said antibodies, antibody fragments or molecular beacons, is detectably labeled.

15. The kit of claim 14, wherein said label is a radiolabel, a fluorophore, a peptide, an enzyme, a quantum dot, or a combination thereof.

16. The kit of claim 15, wherein said label is a quantum dot (QD).

17. The kit of claim 16, wherein said quantum dot is a CdSe crystal and wherein said crystal varies in size between about 1 and 9 nm.

18. The kit of claim 17, wherein said software package comprises a library of emitted spectra from a sample obtained from a subject with MDS and wherein said spectra is of quantum dot labeled antibodies, antibody fragments or molecular beacons.

19. The kit of claim 18, wherein said software further comprises instructions for carrying out a method of diagnosing a subject with a myelodysplastic syndrome (MDS), comprising analyzing predictive parameters in a blood sample of said subject; assigning a numerical value corresponding to a measure of each of said predictive parameters; comparing said value to the value obtained for said predictive parameters from a control group; and assigning a numerical score reflecting the variance between the mean values obtained for said predictive parameters in said subject and that obtained for the same predictive parameters in said control group, wherein said predictive parameters comprise: a measure of polymorphic neutrophil (PMN) granularity and the expression of CD66, CD11a, CD10, and 116 in cells of said blood sample, and wherein said numerical score provides indication of the presence or absence of said syndrome in said subject.

20. The kit of claim 13, further comprising one or more of: packaging materials, instructions for using the components of said kit, one or more containers for holding said components, standards for calibrating fluorescence detection of antibody, antibody fragment or molecular beacon.

21. The kit of claim 13, further comprising at least one standard, obtained from a subject, or pool of subjects, without MDS.

22. The kit of claim 13, further comprising at least one standard, obtained from a subject, or pool of subjects, with MDS.

23. The kit of claim 13, wherein said kit is used for detecting the presence of MDS, quantifying the severity of MDS, evaluating efficiency of treatment regimen for MDS or a combination thereof.

24. The kit of claim 13, further comprising a software package, wherein said software package compares a value obtained from the test subject with a standard to diagnose MDS.

25. The kit of claim 13, wherein said myelodysplastic syndrome (MDS) is refractory cytopenia with multilineage dysplasia (RCMD) refractory anaemia (RA), acquired idiopathic sideroblastic anemia (AISA), refractory anaemia with ring sideroblasts (RARS), refractory anaemia with excess blasts (RAEB), refractory anaemia with excess blasts in transformation (RAEB-t), chronic myelomonocytic leukaemia (CMML), atypical chronic myelogenous leukemia (aCML), erythroid dysplasia, thrombocytosis, hypolobated micromegakaryocytic hyperplasia, or a combination thereof.

* * * * *